United States Patent [19]

Willms et al.

[11] Patent Number: 4,492,598
[45] Date of Patent: Jan. 8, 1985

[54] SULFONYLUREAS HAVING HETEROCYCLIC SUBSTITUENTS, AND THEIR USE IN AGRICULTURE

[75] Inventors: Lothar Willms, Unkel; Thomas Hüttelmaier; Hilmar Mildenberger, both of Kelkheim; Klaus Bauer, Rodgau; Helmut Bürstell, Frankfurt am Main; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 406,076

[22] Filed: Aug. 6, 1982

[30] Foreign Application Priority Data

Aug. 8, 1981 [DE] Fed. Rep. of Germany ....... 3131489

[51] Int. Cl.³ ................. C07D 251/52; C07D 251/46; C07D 251/70; A01N 43/70
[52] U.S. Cl. ........................................ 71/93; 544/211; 544/206; 544/208; 544/197
[58] Field of Search ............... 544/197, 206, 208, 211; 71/93

[56] References Cited

U.S. PATENT DOCUMENTS 4,127,405 11/1978 Levitt ................... 544/212

Primary Examiner—John M. Ford
Attorney, Agent, or Firm—Curtis, Morris & Safford

[57] ABSTRACT

Compounds of the formula

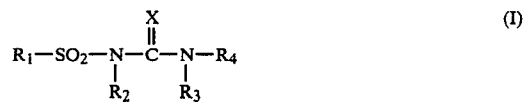

wherein $R_1$ is (among others) (halo)cycloalkyl or (halo)cycloalkenyl, $R_2$ and $R_3$ are preferably hydrogen, X is preferably oxygen and $R_4$ is substituted pyrimidyl or s-triazinyl, are valuable herbicides and growth regulators.

18 Claims, No Drawings

SULFONYLUREAS HAVING HETEROCYCLIC SUBSTITUENTS, AND THEIR USE IN AGRICULTURE

It has already been disclosed that phenylsulfonylureas having heterocyclic substituents, such as, for example, N-(4-chloro-6-i-propylamino-1,3,5-triazin-2-yl)-N-i-propyl-N'-(4-chlorophenylsulfonyl)urea, have herbicidal or plant-growth regulating properties (cf. Netherlands Patent 121,788, German Offenlegungsschrift No. 2,715,786, European Pat. Nos. 1,485, 1,514, 1,515, 4,163, 7,687, 9,419, 10,560, 23,140, 23,141 and 23,422).

It has now been found that cyclo- and bicycloalkylsulfonylureas having heterocyclic substituents are also suitable as herbicides and plant-growth regulators.

Thus the present invention relates to compounds of the formula I

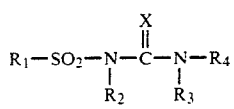

wherein $R_1$ denotes a saturated cycloaliphatic radical having 3 to 12 C atoms or a cycloaliphatic radical having 5-12 C atoms, which is monounsaturated or polyunsaturated and all of which can optionally be substituted by up to 4 halogen atoms and/or by one or more $(C_1-C_4)$-alkyl or halogenoalkyl (the latter having 1-3 halogen atoms) or by a $(C_1-C_4)$-alkoxycarbonyl radical; a bicyclic saturated or monounsaturated or diunsaturated aliphatic radical having 7 to 12 C atoms, which can optionally carry up to 6 halogen atoms or one or more $(C_1-C_4)$-alkyl radicals or in which a $CH_2$ bridge can be replaced by oxygen, $R_2$ and $R_3$ denote H or $(C_1-C_4)$-alkyl, X denotes O or S, $R_4$ denotes a six-membered heterocyclic ring containing 2-3 nitrogen atoms, which is optionally substituted 1-3 times by halogen, $NO_2$, CN, CHO, $(C_1-C_4)$-alkylamino, $(C_1-C_4)$-dialkylamino, a $(C_1-C_4)$-alkyl radical (which is optionally substituted by halogen, $(C_1-C_3)$-alkoxy, $(C_1-C_3)$-alkylthio, $(C_1-C_3)$-alkylamino, $(C_1-C_3)$-dialkylamino or $(C_1-C_4)$-alkoxycarbonyl), a $(C_1-C_4)$-alkoxy or $(C_1-C_4)$-alkylthio radical (which are optionally substituted by halogen or $(C_1-C_4)$-alkoxycarbonyl), or $(C_1-C_4)$-alkoxycarbonyl, and, if $R_2$ denotes hydrogen, their physiologically tolerated salts with bases.

"Halogen" preferably denotes fluorine, chlorine or bromine.

Those compounds are particularly preferred in which $R_1$ denotes a saturated or monounsaturated $(C_5-C_8)$-cycloaliphatic or $(C_7-C_8)$-bicyclic radical which is unsubstituted or substituted once or more times by Cl or $CH_3$, it being possible for Cl to be present, preferably, up to three times and $CH_3$ up to 9 times.

Examples of sulfonylureas having heterocyclic substituents of the formula I according to the invention which may be mentioned in addition to the compounds described in the experimental section are the following: N-[(4-methoxy-6-methyl-1,3,5-triazin-2-yl)aminocarbonyl]-1,2-dichlorocyclohexylsulfonamide; N-[(2,6-dimethyl-5-chloropyrimidin-2-yl)aminocarbonyl]-3-bromo-1-cyclohexenylsulfonamide; N-[(4-methyl-6-methylthio-1,3,5-triazin-2-yl)aminocarbonyl]-1,3-cyclohexadienylsulfonamide; N-[(4-methyl-6-dimethylamino-1,3,5-triazin-2-yl)-aminocarbonyl]-2-chlorocyclopentylsulfonamide; N-[(-5,6-dimethyl-1,2,4-triazin-3-yl)aminothiocarbonyl]-1-cyclopentenylsulfonamide; N-[(-4,6-dimethoxy-5-chloropyrimidin-2-yl)methylaminocarbonyl]-1-cyclopentenylsulfonamide; N-[(-4,5-dimethyl-6-methoxypyrimidin-2-yl)aminocarbonyl]-1-cycloheptenylsulfonamide; N-[(4-methyl-5-nitro-6-chloropyrimidin-2-yl)aminocarbonyl]-2-chlorocyclooctylsulfonamide; N-[(4-methoxycarbonyl-6-methyl-1,3,5-triazin-2-yl)aminocarbonyl]-1-cyclooctenylsulfonamide; N-[(4-chloro-6-isopropylamino-1,3,5-triazin-2-yl)aminocarbonyl]-1-cyclooctenylsulfonamide; N-[(-4-trifluoromethyl-6-methylpyrimidin-2-yl)aminocarbonyl]-3-cyclohexenylsulfonamide; N-[(4,6-di-methylmercapto-1,3,5-triazin-2-yl)aminocarbonyl]-cyclohexylsulfonamide; N-[(4-methylpyrimidin-2-yl)aminocarbonyl]-3,4-dichlorocyclohexylsulfonamide; N-[(4-methoxy-5-n-butyl-6-methylpyrimidin-2-yl)aminocarbonyl]-1,2-dibromocyclohexylsulfonamide; N-[(4-methoxycarbonylmethoxy)-6-methylpyrimidin-2-yl)aminocarbonyl]-1-cyclohexenylsulfonamide, sodium salt; N-[(4-methoxy-6-methyl-1,3,5-triazin-2-yl)methylaminocarbonyl]-1-cyclohexenylsulfonamide; N-[(4-methoxy-6-methylpyrimidin-2-yl)aminocarbonyl]-cyclopentylsulfonamide; N-[(4-ethyl-6-methoxy-1,3,5-triazin-2-yl)aminocarbonyl]-cyclopentylsulfonamide; N-[(4-methoxy-6-methylpyrimidin-2-yl)aminocarbonyl]-1,2-dichlorocyclopentylsulfonamide; N-[(4-methoxy-6-methylpyrimidin-2-yl)-aminocarbonyl]-2-chlorocyclopentylsulfonamide; N-[(4,6-dimethoxy-1,3,5-triazin-2-yl)aminocarbonyl]-2-chlorocyclodecylsulfonamide; N-[(4-methoxy-6-methylpyrimidin-2-yl)aminocarbonyl]-3-chlorobicyclo[2.2.1]hept-2-ylsulfonamide; N-[(4-methoxy-6-methyl-1,3,5-triazin-2-yl)-aminocarbonyl]-bicyclo[2.2.1]hept-5-en-2-ylsulfonamide; N-[(4,6-dimethylpyrimidin-2-yl)aminocarbonyl]-bicyclo[2.2.2]oct-2-ylsulfonamide; N-[(4-methoxy-6-methyl-1,3,5-triazin-2-yl)aminocarbonyl]-2,3,3-trimethylbicyclo[2.2.1]-hept-2-ylsulfonamide; N-[(4-methoxy-6-methylpyrimidin-2-yl)aminocarbonyl]bicyclo[2.2.1]hept-2-ylsulfonamide; N-[(5,6-dimethyl-1,2,4-triazin-3-yl)aminocarbonyl]-4,5-dichlorobicyclo[2.2.1]heptylsulfonamide; N-[(4,6-dimethylpyrimidin-2-yl)aminocarbonyl]-2,2,5,5-tetramethyl-3-cyclohexenylsulfonamide; N-[(4-methoxymethyl-6-methyltriazin-2-yl)aminocarbonyl]-2-chlorocyclohexenylsulfonamide; N-[(4-methoxy-6-methylpyrimidin-2-yl)aminocarbonyl]-2-chloro-3-methyl-4-cyclohexenylsulfonamide; N-[(4,6-dimethyl-1,3,5-triazin-2-yl)aminocarbonyl]-2,4,5-trichloro-3-methylcyclohexylsulfonamide; N-[(4-methoxy-6-methylpyrimidin-2-yl)aminocarbonyl]-2-chlorocyclooctylsulfonamide; N-[(4,6-dimethyl-1,3,5-triazin-2-yl)aminocarbonyl]-cyclopropylsulfonamide; N-[(4-methoxy-6-methyl-1,3,5-triazin-2-yl)aminocarbonyl]-2-methyl-5-isopropylcyclohexylsulfonamide; N-[(4,6-dimethyl-pyrimidin-2-yl)aminocarbonyl]bicyclo[3.2.2]non-2-ylsulfonamide.

The new compounds of the general formula I can be synthesized from starting materials known in themselves or which have been prepared by known processes. The processes for preparation comprise (a) reacting compounds of the formula

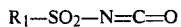

or

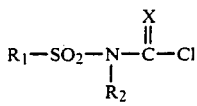

with compounds of the formula

      (IV)

or (b) reacting compounds of the formula

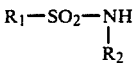      (V)

with compounds of the formula $S=C=N-R^4$      (VI)

or

      (VII)

wherein $R_3$ denotes $(C_1-C_4)$-alkyl,
or (c) reacting compounds of the formula

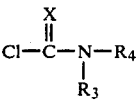      (VIII)

wherein $R_5$, $R_6$ and $R_7$ denote hydrogen, halogen or $(C_1-C_4)$-alkyl with compounds of the formula

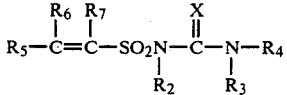      (IX)

wherein $R_8$ to $R_{13}$ represent hydrogen, halogen or $CH_3$ and one of the radicals $R_9$ to $R_{12}$ can also be $(C_2-C_4)$-alkyl or $(C_1-C_4)$-alkoxycarbonyl or $R_8$ and $R_{13}$ together represent a $(C_1-C_6)$-alkylene group, in which a —$CH_2$— group can also be replaced by oxygen, and, if desired, converting the compounds of the formula I obtained into other compounds of the formula I by splitting off hydrogen halide, adding halogen or hydrogen onto multiple bonds when present, alkylating in the $R_2$ position or forming a salt.

In respect of (a) the reaction of the compounds II or III and IV is preferably carried out in inert aprotic solvents such as, for example, acetonitrile, dichloromethane, toluene, tetrahydrofuran or dioxane at temperatures between 0° C. and the boiling point of the solvent. When starting materials of the formula III are used, the reaction is carried out in the presence of an acid acceptor such as, for example, potassium carbonate, pyridine or triethylamine.

In respect of (b) the reaction of the compounds V with VI or VII is also carried out in the abovementioned inert solvents with the addition of basic compounds such as, for example, potassium carbonate, pyridine or triethylamine at temperatures between 0° C. and the boiling point of the solvent.

In respect of (c) the reaction of the compounds VIII and IX is preferably carried out in inert solvents such as, for example, toluene, xylene, dioxane or dichloromethane at temperatures between room temperature and the boiling point of the solvent. If appropriate, the reaction can be carried out in the presence of catalysts such as, for example, aluminum trichloride, or in autoclaves under elevated pressure.

The subsequent splitting off of hydrogen halide (HCL, HBr) from radicals $R_1$ containing halogen is carried out in a known manner, for example with alkali metal alcoholate, alcoholic sodium hydroxide or potassium hydroxide solution, triethylamine or other agents which split off acid, optionally in the presence of a further inert solvent or diluent (for example toluene) at temperatures between room temperature and the boiling point.

Halogen ($Cl_2$, $Br_2$), hydrogen halide or hydrogen can be added onto multiple bonds in the $R_1$ position, which are present or which are formed subsequently, under normal pressure or under elevated pressure, where appropriate, in the presence of a catalyst, for example Pd/charcoal or Raney nickel in a manner which is also known and thus, if desired, provide new compounds of the formula I. The bromination or chlorination is carried in inert organic solvents such as, for example, dichloromethane or chloroform, with irradiation, for example with ultraviolet light, or in the presence of compounds which decompose to give radicals, for example, azodiisobutyronitrile, at temperatures between 0° C. and the boiling point of the solvent. The addition of hydrogen halide is carried out in the presence of inert solvents (for example toluene) using gaseous HCl or HBr at low temperatures, optionally in the presence of a peroxide catalyst.

For subsequent alkylation in the $R_2$ position, the reaction is preferably carried out in inert solvents such as, for example, dioxane or dimethylformamide, with addition of an inorganic base, for example sodium hydride or potassium carbonate, at temperatures from 20° C. up to the boiling point of the solvent. Examples of alkylating agents used are dimethyl sulfate, methyl iodide or ethyl bromide.

Compounds of the formula I, in which $R_2$ denotes hydrogen, can form salts in which H is replaced by a cation which is suitable for agriculture. These salts are generally salts of metals, ammonium or organic amines and are preferably prepared in inert solvents such as, for example, water, methanol or acetone at temperatures of 20°–100°. Examples of suitable bases for preparing the salts according to the invention are potassium carbonate, ammonia or ethanolamine.

The starting materials of the formula IV are known or can be prepared by processes which are known in principle, for example by cyclization of appropriate guanidine derivatives with appropriate substituted 1,3-diketones (cf. for example "The Chemistry of Heterocyclic Compounds", vol. XVI (1962) and Supplement I (1970)) or by derivatization of cyanuric chloride (cf. for example "The Chemistry of Heterocyclic Compounds", L. Rapoport: "s-Triazines and Derivatives" (1959)).

The sulfonyl isocyanates of the formula II are also mostly known or can be prepared in a simple manner by processes which are known in principle (cf. German Auslegeschriften Nos. 1,211,165, 1,230,016 and 1,297,601).

The sulfonylcarbamoyl or sulfonylthiocarbamoyl chlorides of the formula III can be prepared by customary methods from the alkali metal salts of the corresponding sulfonamides of the formula V, which are known from the literature, by reaction with phosgene or thiophosgene.

The isothiocyanates of the formula VI which are required for the reactions according to process (b) are known or are accessible by known processes (cf. Tetrahedron 29, 691 (1973); Japan Kokai Sho-51-143686).

The same applies to the heterocyclic carbamoyl chlorides and thiocarbamoyl chlorides of the formula VII (cf. for example German Auslegeschriften Nos. 1,149,718 and 2,238,870).

The $\alpha,\beta$-unsaturated sulfonylureas of the formula VIII are described in the Patent Application Nos. P 31 11 451.2.

The heterocyclic sulfonylurea derivatives according to the invention exhibit an excellent herbicidal activity and a very good selectivity in important crops which are grown on a large scale. Thus they are suitable for the selective control of dicotyledonous and graminaceous annual and perennial weeds, especially in crops of agricultural importance such as, for example, wheat, barley, rye, rice, corn, sugar beet and soya bean. In this context, it is immaterial whether the substances are applied by pre-sowing, pre-emergence or post-emergence spraying. If the compounds according to the invention are applied to the surface of the earth in a pre-sowing or pre-emergence process and before the weed plants have germinated, the sprouting of the seedlings is not prevented. The weeds grow to the cotyledon stage but then stop growing and finally die completely after 3–5 weeks. When the active compounds are applied to the green parts of the plant in a post-emergence process, again a drastic termination of growth occurs rapidly after treatment and the weed plants remain at the stage of growth present at the time of application or die completely after a certain time so that, by this means, competition by weeds, which is injurious to the crop plants, is removed very early and permanently.

Furthermore, the substances according to the invention exhibit outstanding growth-regulating properties for crop plants. They intervene to regulate the plants' own metabolism and can thus be employed to produce specific effects on the plant constituents and to facilitate harvesting, such as, for example, by inducing desiccation and growth shortening. Moreover, they are suitable for general control and inhibition of undesired vegetative growth without at the same time killing the plants. Inhibition of vegetative growth makes a large contribution to many monocotyledonous and dicotyledonous crops, since, by this means, storage can be decreased or completely avoided. The growth-regulating effect of the compounds as growth inhibitors of cereals, corn, soya bean, cotton and lawns and their ability to increase the content of desired constituents, such as carbohydrates and protein in crop plants, should be particularly emphasized. Finally, the compounds show a very great improvement of the fruit abscission, specially for citrous fruits, or reduction of the retaining power.

Thus the invention also relates to herbicidal or growth-regulating agents which contain a compound of the formula I in combination with customary formulating auxiliaries and inert compounds and their use in agriculture.

The agents according to the invention generally contain the active compounds of the formula I to an extent of 2 to 95% by weight. They can be used in the customary formulations as powders for spraying, emulsifiable concentrates, sprayable solutions, dusting agents or granules.

The powders for spraying are formulations which can be uniformly dispersed in water and which contain, in addition to the active compound and a diluent or inert compound, wetting agents, for example polyoxyethylated alkylphenols, polyoxyethylated fatty alcohols, alkylsulfonates or alkylphenylsulfonates and dispersants, for example sodium ligninsulfonate, sodium 2,2'-dinaphthylmethane-6,6'-disulfonate, sodium dibutylnaphthalenesulfonate or also sodium oleylmethyltaurate.

Emulsifiable concentrates are prepared by dissolving the active compound in an organic solvent, for example butanol, cyclohexanone, dimethylformamide, xylene or also high-boiling aromatic compounds or hydrocarbons with the addition of one or more emulsifiers. Examples of emulsifiers which can be used are:

Calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, condensation products of propylene oxide and ethylene oxide, condensation products of fatty alcohols, propylene oxide and ethylene oxide, alkyl polyethers, sorbitan fatty acid esters, polyoxyethylene sorbitol fatty acid esters or polyoxyethylene sorbitol esters.

Dusting agents are obtained by milling the active compound with finely divided solid materials, for example talc, natural clays, such as kaolin, bentonite, pyrophillite or diatomaceous earths.

Granules can be prepared either by spraying the active compound onto absorbent granules of inert material or by applying concentrates of the active compounds, using adhesives, for example, polyvinyl alcohol, sodium polyacrylate or also mineral oils, onto the surface of vehicles, such as sand or kaolinite, or of granules of inert material. Suitable active compounds can also be prepared in the manner customary for the preparation of granulated fertilizers, if desired mixed with fertilizers.

For herbicidal agents, the concentrations of the active compounds in the commercial formulations can vary.

In powders for spraying, the concentration of active compound varies, for example, between about 10% and 80%, the remainder comprising the formulation additives mentioned above. In emulsifiable concentrates, the concentration of active compound can also be about 10% to 80%. Formulations as dusts contain about 2–20%. In granules, the content of active compound depends, to some extent, on whether the active compound is liquid or solid and which granulating auxiliaries, fillers and the like are used.

The commercial concentrates when used as herbicides are, when appropriate, diluted in a customary manner, for example using water for powders for spraying and emulsifiable concentrates. Formulations as dusts and granules and spraying solutions are not further diluted with inert substances before use. The amount which is required to be used varies with the outside conditions, such as temperature, humidity and the like.

In general, it is between 0.01 and 10 kg/hectare, preferably about 0.1 to 5.0 kg/hectare of active compound.

It can be advantageous for some areas of use to use the new herbicides together with one or more herbicides, for example as a tank mixture or in the form of a ready-to-use formulation in order to obtain further advantageous effects.

The active compounds according to the invention can be combined with other herbicides, insecticides and fungicides.

Concentrations between 0.01 and 1.25 kg/hectare are suitable for use as growth regulators. Aqueous dispersions of powders for spraying or dilutions of emulsifiable concentrates are preferably used. These are used post-emergence. The preferred crops are corn and tobacco.

PREPARATION EXAMPLES

EXAMPLE 1

N-[(4-Methoxy-6-methylpyrimidin-2-yl)aminocarbonyl]-2-chlorocyclohexylsulfonamide 41.7 g (0.3 mole) of 2-amino-4-methoxy-6-methylpyrimidine were suspended in 500 ml of dichloromethane and a solution of 71.5 g (0.32 mole) of 2-chlorocyclohexylsulfonyl isocyanate in 200 ml of dichloromethane was added dropwise at 0° C. The reaction mixture was stirred a further 18 hours at room temperature, cooled to 0° C. and n-hexane was added. The precipitated reaction product was filtered off with suction and washed with n-hexane.

84.9 g (78% of theory) of N-[(4-methoxy-6-methylpyrimidin-2-yl)aminocarbonyl]-2-chlorocyclohexylsulfonamide were obtained, having a melting point of 145°–148°.

EXAMPLE 2

N-[(4-Methoxy-6-methylpyrimidin-2-yl)aminocarbonyl]-1-cyclohexenylsulfonamide 36.2 g (0.1 mole) of N-[(4-methoxy-6-methylpyrimidin-2-yl)aminocarbonyl]-2-chlorocyclohex-1-ylsulfonamide (see Example 1) were suspended in 300 ml of methanol and 8 g (0.2 mole) of sodium hydroxide dissolved in 40 ml of water were added at room temperature. The reaction mixture was then stirred under reflux for 8 hours, evaporated in vacuo and taken up in 250 ml of water. After filtration and acidification with 2N HCl to pH 5, extraction was carried out with ethyl acetate and then the extracts were dried over sodium sulfate and evaporated. After adding n-hexane, 17.2 g (52.7% of theory) of N-[(4-methoxy-6-methylpyrimidin-2-yl)aminocarbonyl]-1-cyclohexenylsulfonamide were obtained, having a melting point of 163°–166° C.

EXAMPLE 3

N-[(4,6-Dimethylpyrimidin-2-yl)aminocarbonyl]-7-oxabicyclo[2.2.1]hept-2-en-6-ylsulfonamide 30.7 g (0.25 mole) of 2-amino-4,6-dimethylpyrimidine were dissolved in 350 ml of dichloromethane and a solution of 52 g (0.26 mole) of 7-oxabicyclo[2.2.1]hept-2-en-6-ylsulfonyl isocyanate (Diels-Alder adduct of vinylsulfonyl isocyanate and furan) in 100 ml of dichloromethane was added at 0° C. with stirring. The mixture was stirred a further 12 hours at room temperature, cooled to 0° C. and n-hexane was added. The precipitated reaction product was filtered off with suction, washed with n-hexane and dried. 73.6 g (90.8% of theory) of N-[(4,6-dimethylpyrimidin-2-yl)aminocarbonyl]-7-oxabicyclo[2.2.1]hept-2-en-6-ylsulfonamide having a melting point of 125°–145° C. were obtained.

EXAMPLE 4

N-[(4-Methylthio-6-methyl-1,3,5-triazin-2-yl)aminocarbonyl]-3 (or 4)-methyl-3-cyclohexenylsulfonamide 7.81 g (0.05 mole) of 2-amino-4-methylthio-6-methyl-1,3,5-triazine were suspended in 150 ml of dichloromethane and a solution of 11.05 g (0.055 mole) of 3 (or 4)-methyl-3-cyclohexen-1-ylsulfonyl isocyanate (mixture of isomers; Diels-Alder adduct of isoprene to vinylsulfonyl isocyanate) in 50 ml of dichloromethane was added at 0° C. The mixture was stirred a further 18 hours at room temperature and was worked up in analogy to Example 1. 13.2 g (74% of theory) of N-[(4-methylthio-6-methyl-1,3,5-triazin-2-yl)aminocarbonyl]-3 (or 4)-methyl-3-cyclohexenylsulfonamide were obtained, having a melting point of 156°–160° C.

EXAMPLE 5

N-[(4,6-Dimethylpyrimidin-2-yl)aminocarbonyl]-2-chlorocycloheptylsulfonamide 14.3 g (0.06 mole) of 2-chlorocycloheptylsulfonyl isocyanate in 100. ml of dichloromethane were initially introduced and 7.4 g (0.06 mole) of 2-amino-4,6-dimethylpyrimidine were added in portions at 0° C. The mixture was stirred initially at 0° C. for 2 hours and then at room temperature for 18 hours. The organic phase was then extracted with 3×40 ml of 2N $H_2SO_4$, washed to neutrality and the organic layer was dried over $Na_2SO_4$. Then 50 ml of n-hexane was added and the solvent was distilled off in vacuo. 13.3 g (61% of theory) of N-[(4,6-dimethylpyrimidin-2-yl)aminocarbonyl]-2-chlorocycloheptylsulfonamide were obtained (viscous oil).

EXAMPLE 6

N-[(4,6-Dimethylpyrimidin-2-yl)aminocarbonyl]-2-chlorocyclodecylsulfonamide 15.4 g (0.05 mole) of 2-chlorododecylsulfonyl isocyanate in 100 ml of dichloromethane were initially introduced and 6.2 g (0.05 mole) of 2-amino-4,6-dimethylpyrimidine were added in portions at 0° C. The mixture was initially stirred at 0° C. for 2 hours and then at room temperature for 18 hours and was then worked up in analogy to Example 5. 15.2 g (71% of theory) of N-[(4,6-dimethylpyrimidin-2-yl)aminocarbonyl]-2-chlorocyclododecylsulfonamide were obtained (pale yellow solid material, melting point 84° C.).

EXAMPLE 7

N-[(4,6-Dimethylpyrimidin-2-yl)aminocarbonyl]-3-chlorobicyclo[2.2.1]hept-2-ylsulfonamide 14.1 g (0.06 mole) of 3-chlorobicyclo[2.2.1]hept-2-ylsulfonyl isocyanate in 100 ml of dichloromethane were initially introduced and 7.4 g (0.06 mole) of 2-amino-4,6-dimethylpyrimidine were added in portions at 0° C. The mixture was initially stirred at 0° C. for 2 hours and then at room temperature for 18 hours and then worked up in analogy to Example 5. 14.1 g (66% of theory) of N-[(4,6-dimethylpyrimidin-2-yl)aminocarbonyl]-3-chlorobicyclo[2.2.1]hept-2-ylsulfonamide were obtained (viscous oil).

The following compounds were, or can be, obtained in an analogous manner

TABLE 1

$$R_1-SO_2-\underset{R_2}{N}-\underset{\parallel}{\overset{O}{C}}-\underset{R_3}{N}-R_4$$

| Example No. | R₁ | R₂ | R₃ | R₄ | Melting point (°C.) |
|---|---|---|---|---|---|
| 8 | 2-chlorocyclohexyl | H | H | 4,6-dimethylpyrimidin-2-yl | 155–163 |
| 9 | " | H | H | 4-methoxy-6-methylpyrimidin-2-yl | 118–123 |
| 10 | " | H | H | 4,6-dimethoxy-2-methylpyrimidin-? | 159–162 |
| 11 | " | H | H | 4,6-dimethoxy-1,3,5-triazin-2-yl | 143–144 |
| 12 | 2-chlorocycloheptyl | H | H | 4-methoxy-6-methyl-1,3,5-triazin-2-yl | glass-like |
| 13 | (CH₂)₆ with CHCl–CH– | H | H | 4,6-dimethylpyrimidin-2-yl | 48–52 (Decomp.) |
| 14 | " | H | H | 4-methoxy-6-methylpyrimidin-2-yl | viscous oil |
| 15 | (CH₂)₁₀ with CHCl–CH– | H | H | 4-methoxy-6-methylpyrimidin-2-yl | 103 |

TABLE 1-continued $$R_1-SO_2-\underset{R_2}{N}-\overset{\overset{O}{\|}}{C}-\underset{R_3}{N}-R_4$$

| Example No. | R₁ | R₂ | R₃ | R₄ | Melting point (°C.) |
|---|---|---|---|---|---|
| 16 | cyclohex-3-enyl | H | H | pyrimidine with OCH₃, CH₃ | 142-144 |
| 17 | cyclohex-1-enyl | H | H | pyrimidine with CH₃, CH₃ | 165-169 |
| 18 | " | H | H | pyrimidine with OCH₃, CH₃ | 150 |
| 19 | " | H | H | pyrimidine with OCH₃, OCH₃ | 159-167 |
| 20 | cyclohept-1-enyl | H | H | pyrimidine with CH₃, CH₃ | viscous oil |
| 21 | " | H | H | pyrimidine with OCH₃, CH₃ | viscous oil |
| 22 | 2-methylcyclohex-1-enyl | H | H | pyrimidine with OCH₃, CH₃ | 195 |
| 23 | " | H | H | pyrimidine with OCH₃, CH₃ | 143 |

TABLE 1-continued $$R_1-SO_2-\underset{R_2}{N}-\underset{\parallel}{\overset{O}{C}}-\underset{R_3}{N}-R_4$$

| Example No. | $R_1$ | $R_2$ | $R_3$ | $R_4$ | Melting point (°C.) |
|---|---|---|---|---|---|
| 24 | " | H | H | pyrimidine with 4-OCH₃, 6-OCH₃, 2-CH₃ | 173–176 |
| 25 | " | H | H | pyrimidine with OC₂H₅, CH₃ | 89–92 |
| 26 | " | H | H | pyrimidine with N(C₂H₅)₂, CH₃ | 161–164 |
| 27 | 4-methyl-cyclohex-2-enyl with COOCH₃ | H | H | pyrimidine with 4-CH₃, 6-CH₃ | 54–57 |
| 28 | " | H | H | pyrimidine with OCH₃, CH₃ | 88–91 |
| 29 | chloro-methyl-norbornyl | H | H | pyrimidine with OCH₃, CH₃ | viscous oil |
| 30 | oxa-norbornenyl-methyl | H | H | pyrimidine with OCH₃, CH₃ | 146–150 |
| 31 | " | H | H | pyrimidine with OCH₃, CH₃ | 135–145 |

TABLE 1-continued $$R_1-SO_2-\underset{R_2}{N}-\overset{\overset{O}{\|}}{C}-\underset{R_3}{N}-R_4$$

| Example No. | R₁ | R₂ | R₃ | R₄ | Melting point (°C.) |
|---|---|---|---|---|---|
| 32 | 1-chloro-2-methylcyclohexenyl | H | H | 4-methoxy-6-methyl-pyrimidin-2-yl (OCH₃, CH₃) | resin |
| 33 | " | H | H | 4,6-dimethyl-pyrimidin-2-yl (CH₃, CH₃) | 152–154 |
| 34 | " | H | H | 4-methoxy-6-methyl-pyridin-2-yl (OCH₃, CH₃) | |
| 35 | 1-bromo-2-methylcyclohexenyl | H | H | 4-methoxy-6-methyl-pyrimidin-2-yl (OCH₃, CH₃) | |
| 36 | 1-chloro-2-methyl-3-methylcyclohexenyl (Cl, CH₃, CH₃) | H | H | 4-methoxy-6-isopropyl-pyrimidin-2-yl (OCH₃, CH₃) | |
| 37 | 1,2-dichlorocyclohexyl (Cl, Cl) | H | H | 4,6-dimethyl-pyrimidin-2-yl (CH₃, CH₃) | 78–80 |
| 38 | " | H | CH₃ | 4-methoxy-6-isopropyl-pyrimidin-2-yl (OCH₃, CH₃) | |
| 39 | 1,2-dibromocyclohexyl (Br, Br) | H | H | 4-methoxy-6-isopropyl-pyrimidin-2-yl (OCH₃, CH₃) | |

TABLE 1-continued

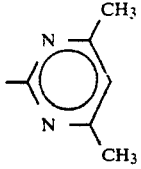

| Example No. | R₁ | R₂ | R₃ | R₄ | Melting point (°C.) |
|---|---|---|---|---|---|
| 40 | " | H | H | (4,6-dimethylpyrimidin-2-yl) | 137–138 |

FORMULATION EXAMPLES

EXAMPLE A

An emulsifiable concentrate was obtained from:
15 parts by weight of active compound
75 parts by weight of cyclohexane as the solvent, and
10 parts by weight of oxyethylated nonylphenol (10 EO) as emulsifier

EXAMPLE B

A wettable powder, which was easily dispersible in water, was obtained by mixing
25 parts by weight of active compound
64 parts by weight of kaolin-containing quartz as inert material
10 parts by weight of potassium ligninsulfonate, and
1 part by weight of sodium oleylmethyltaurate as wetting agent and dispersant
and milling in a pinned disk mill.

EXAMPLE C

A dusting agent was obtained by mixing
10 parts by weight of active compound and 90 parts by weight of talc as inert material
and grinding in a beater mill.

EXAMPLE D

Granules are composed of, for example,
about 2–15 parts by weight of active compound and
about 98–85 parts by weight of inert granular materials, such as, for example, attapulgite, pumice and quartz sand.

BIOLOGICAL EXAMPLES

(a) Herbicidal activity

The damage to the weed plants and the tolerance by the crop plants were classified by scoring from 0–5.
The significance of these scores is as follows:
0 = no effect (damage)
1 = 0–20% effect
2 = 20–40% effect
3 = 40–60% effect
4 = 60–80% effect
5 = 80–100% effect
The abbreviations have the following meanings:
LOM = ryegrass (lolium multiflorum)
STM = starwort (stellaria media)
SIA = charlock (sinapis arvensis)
AS = active substance

1. Pre-emergence process

Seeds or pieces of rhizomes of monocotyledonous and dicotyledenous weeds were scattered on loam and covered with soil. The compounds according to the invention formulated as wettable powders were applied in the form of aqueous suspensions or emulsions to the surface of the soil. The amount of water used per pot corresponded on conversion to 600–800 l/hectare. After the treatment, the test pots were placed in a glasshouse and the test plants were cultivated under good conditions for growth (temperature: about 23° C.; relative atmospheric humidity 60–80%). After about 3 weeks, the plant damage was scored visually. Untreated controls served as a comparison in this test.

The pre-emergence results are compiled in Table 2. It is apparent that the compounds according to the invention exhibit a good herbicidal activity against both monocotyledenous and also dicotyledenous weeds when the active compounds were administered in a pre-emergence process.

TABLE 2

Pre-emergence effect of the compounds according to the invention against monocotyledenous and dicotyledenous weeds

| Example | Dose of AS kg/hectare | LOM | STM |
|---|---|---|---|
| 1 | 2.5 | 3 | 4 |
| 9 | 2.5 | 2 | 3 |
| 10 | 2.5 | 3 | 2 |
| 16 | 2.5 | 5 | 5 |
| 19 | 2.5 | 5 | 5 |
| 3 | 2.5 | 4 | 4 |
| 30 | 2.5 | 5 | 5 |
| 31 | 2.5 | 5 | 4 |
| 28 | 2.5 | 2 | 3 |
| 32 | 2.5 | 5 | 5 |
| 33 | 2.5 | 5 | 5 |
| 37 | 2.5 | 5 | 5 |

2. Post-emergence process

Seeds of monocotyledenous and dicotyledenous weeds were sown in pots and raised in a glasshouse under good conditions for growth. A few weeks after sowing, the test plants were treated at the three-leaf stage. The products according to the invention, which were formulated as powders for spraying or as emulsion concentrates, were sprayed onto the green parts of the plants at various dosages and, after about 3 weeks standing in a glasshouse under optimum conditions for growth (temperature: about 23° C.; relative atmospheric humidity 60–80%), the effect of the products were scored visually in comparison to untreated controls.

The agents according to the invention showed good herbicidal effectiveness against a wide spectrum of economically important annual and perennial weeds and unwanted grasses (Table 3):

TABLE 3

Herbicidal activity of the compounds according to the invention against monocotyledenous and dicotyledenous weeds in the post-emergence process

| Product | Dose of AS kg/hectare | LOM | SIA |
|---|---|---|---|
| 9 | 2.5 | 1 | 5 |
| 10 | 2.5 | 3 | 4 |
| 19 | 2.5 | 5 | 5 |
| 3 | 2.5 | 3 | 5 |
| 30 | 2.5 | 4 | 5 |
| 31 | 2.5 | 5 | 5 |
| 27 | 2.5 | 0 | 4 |
| 32 | 2.5 | 5 | 5 |
| 33 | 2.5 | 5 | 5 |
| 37 | 2.5 | 5 | 5 |

(b) Plant-growth regulating action

3. Inhibition of growth of cereals

In dish trials in a glasshouse, young cereal plants (wheat, barley and rye) in the 3-leaf stage were sprayed until dripping wet with the compounds indicated in Table 1 in the concentrations of active compound mentioned (kg/hectare). 2-Chloroethyltrimethylammonium chloride was employed as the comparison compound. After the untreated control plants had grown to a height of about 55 cm, the added growth of all plants was measured and the growth inhibition was calculated as a percentage of the added growth of the control plants. In addition, the phytotoxic activity of the compounds was observed. The results are compiled in Table 4. For the report of growth inhibition, 100% denotes a standstill in growth and 0% denotes a growth corresponding to that of the untreated control plants.

TABLE 4

| | Inhibition of growth of cereals | | | |
|---|---|---|---|---|
| Compound according to Example | Concentration used (kg/hectare) | Growth inhibition in % Wheat | Barley | Rye | Phytotoxic activity |
| 3 | 0.62 | 22 | 24 | 22 | no |
|   | 0.31 | 11 | 21 | 18 | damage |
| 28 | 1.25 | 19 | 18 | 15 | no damage |
| 19 | 1.25 | 15 | 10 | 11 | no damage |
| Comparison: (2-Chloroethyl)trimethylammonium chloride | 2.50 | 27 | 8 | 10 | no |
| | 1.25 | 23 | 0 | 0 | damage |

4. Inhibition of growth of bush beans 10-15 cm bush beans were sprayed until dripping wet with the formulations of the active compounds. After 2 weeks, the added growth was measured and the growth inhibition was calculated as a percentage of the added growth of the control plants. The results are compiled in Table 5.

TABLE 5

| Inhibition of growth of bush beans | | | |
|---|---|---|---|
| Compound according to Example | Concentration used (kg/hectare) | Growth inhibition in % | Phytotoxic action |
| 3 | 0.62 | 40 | no |
| Comparison: | 0.34 | 20 | damage |
| CH₂—CO—NH—N(CH₃)₂ / CH₂—COOH | 2.50 | 34 | no damage |

$$\begin{array}{l} CH_2-CO-NH-N \diagup{CH_3} \\ | \qquad\qquad\qquad \diagdown CH_3 \\ CH_2-COOH \end{array}$$

5. Inhibition of growth of lawns

A lawn mixture, which contained 5 representative species, was, after three cutbacks, sprayed until dripping wet with a formulation of an active compound. After 3-4 weeks, the added growth was measured and the growth inhibition was calculated as a percentage of the added growth of the control plants. 100% denotes a standstill in growth and 0% denotes growth corresponding to that of the untreated control plants.

TABLE 6

| | Inhibition of growth of lawns | | |
|---|---|---|---|
| Compound according to Example | Concentration used (kg/hectare) | Growth inhibition in % | Phytotoxic action |
| 3 | 0.62 | 82 | no |
| Comparison: | 0.31 | 70 | damage |
| Maleic hydrazide | 2.50 | 60 | severe damage |

6. Increase in the sugar content of sugarcane

Procedure

Sugarcane plants were raised under glasshouse conditions at 25°-35° C. and about 65% atmospheric humidity. Various amounts of the formulated agents were suspended in water which additionally contained about 0.25% by weight of a surface active agent (nonylphenol).

In each case, 0.3 ml of the suspension was applied with the aid of a spray in the region of the spindle at the level of the last visible leaf blade ("dewlap") (10 plants per concentration). On harvesting after 3 weeks, the leaves of both the treated plants and also of the untreated controls were removed and the internodes were analyzed in groups for their sucrose content. The results are presented in Table 7.

TABLE 7

| Compound according to Example | Concentration used (kg/hectare) | Sugar content in % at harvesting |
|---|---|---|
| 3 | 0.62 | 145 |
| 19 | 0.62 | 239 |
| Control | | 100 |

7. Stimulation of the liberation of ethylene

Calamondine oranges were immersed in a solution of active compound containing 2,000 ppm of active compound for 2 minutes. The ethylene produced by the fruit was then found each day for 5 days by gas chromatography.

The results in Table 8 represent mean values from a total of 3 test series.

TABLE 8

| Compound according to Example | Ethylene production (relative units) 1-5 days overall |
|---|---|
| Control | 2.4 |
| 3 | 12.4 |
| 10 | 9.0 |
| Comparison: Glyoxime | 3.8 |

The compounds according to the claim showed a significantly higher effect on the liberation of ethylene, both initially and long-term, than the comparison agent. The overall amount of ethylene produced also clearly exceeded that of the comparison agent. Since ethylene, which is also produced by the plant, is involved in the processes of ripening and abscission to a determining extent, the test serves to demonstrate the accelerated and comprehensive formation of separating tissue, which is induced by the compounds according to the application, and thus the initiation of the process of abscission.

We claim:

1. A compound of the formula I $$R_1-SO_2-N(R_2)-\overset{X}{\underset{\|}{C}}-N(R_3)-R_4$$

wherein $R_1$ is a saturated cycloaliphatic radical having 3 to 12 C atoms or a cycloaliphatic radical having 5-12 C atoms, which is monounsaturated and all of which can optionally be substituted by up to 4 halogen atoms, $(C_1-C_4)$-alkyl, halogenoalkyl of 1-3 halogen atoms or $(C_1-C_4)$-alkoxycarbonyl; a bicyclic saturated or monounsaturated aliphatic radical having 7 to 12 C atoms, optionally substituted by up to 6 halogen atoms or $(C_1-C_4)$-alkyl, or in which a $CH_2$ bridge can be replaced by oxygen, $R_2$ and $R_3$ are the same or different and each may be H or $(C_1-C_4)$-alkyl, X is O or S, $R_4$ is a 1,3,5-triazine optionally substituted 1-2 times by halogen, $NO_2$, CN, CHO, $(C_1-C_4)$-alkylamino, $(C_1-C_4)$-dialkylamino, $(C_1-C_4)$-alkyl which is optionally substituted by halogen, $(C_1-C_3)$-alkoxy, $(C_1-C_3)$-alkylthio, $(C_1-C_3)$-alkylamino, $(C_1-C_3)$-dialkylamino $(C_1-C_4)$-alkoxycarbonyl, $(C_1-C_4)$-alkoxy which is optionally substituted by halogen or $(C_1-C_4)$-alkoxycarbonyl, or $(C_1-C_4)$-alkylthio which is optionally substituted by halogen or $(C_1-C_4)$-alkoxycarbonyl, or $(C_2-C_4)$-alkoxycarbonyl, and, if $R_2$ denotes hydrogen, its physiologically tolerated salt with base.

2. A compound as claimed in claim 1, wherein $R_2$ and $R_3$ denote hydrogen and X is oxygen.

3. A compound as claimed in claim 1 or 2, wherein $R_1$ is a cycloalkyl radical having 6-12 C atoms which is substituted by chlorine or bromine.

4. A compound as claimed in claim 1 or 2, wherein $R_1$ is a cyclohexenyl, methylcyclohexenyl or chlorocyclohexenyl radical.

5. A compound as claimed in claim 1 or 2, wherein $R_1$ is a cycloheptenyl or oxabicyclo[2.2.1]heptenyl radical.

6. A compound as claimed in claim 1 or 2, wherein $R_1$ is a chlorobicyclo[2.2.1]heptyl radical.

7. A compound as claimed in claim 1, wherein $R_4$ is an s-triazine ring which is substituted in the 4- and 6-position by methyl and/or methoxy.

8. The compound of the formula

[structure: cyclohexenyl-SO₂-NH-CO-NH-(triazine with OCH₃ and CH₃ substituents)]

9. The compound of the formula

[structure: cyclohexenyl-SO₂-NH-CO-NH-(triazine with OCH₃ and CH₃ substituents)]

10. A herbicidal agent having an effective content of a compound as claimed in claim 1 in combination with a carrier therefor.

11. A plant-growth regulating agent having an effective content of a compound as claimed in claim 1 in combination with a carrier therefor.

12. A process for controlling undesired plant growth which comprises applying an effective amount of a compound as claimed in claim 1 to the plants to be controlled or to the area of cultivation.

13. A process for regulating the growth of crop plants which comprises applying an effective amount of a compound as claimed in claim 1 to the plants to be controlled or to the area of cultivation.

14. The compound as claimed in claim 1, which is N-[(4-methoxy-6-methyl-1,3,5-triazin-2-yl)amino-carbonyl]-7-oxabicyclo[2.2.1]hept-2-en-6-ylsulfon-amide.

15. A herbicidal agent containing a compound as claimed in claim 14 in combination with a carrier therefor.

16. A plant-growth regulating agent having an effective content of a compound as claimed in claim 14 in combination with a carrier therefor.

17. A process for regulating the growth of crop plants which comprises applying an effective amount of a compound according to claim 14 to the plants to be controlled or the area of cultivation.

18. A process for regulating the growth of crop plants which comprises applying an effective amount of a compound according to claim 14 to the plants to be treated.

* * * * *